United States Patent
Graumann et al.

(10) Patent No.: US 6,678,353 B2
(45) Date of Patent: Jan. 13, 2004

(54) APPARATUS AND METHOD FOR DETERMINING THE SPATIAL RELATIONSHIP OF X-RAY DATASETS REGISTERED INDEPENDENTLY OF ONE ANOTHER

(75) Inventors: Rainer Graumann, Hoechstadt (DE); Joachim Hey, Nuremberg (DE)

(73) Assignee: Siemens Aktiengesellschaft, Münich (DE)

( * ) Notice: Subject to any disclaimer, the term of this patent is extended or adjusted under 35 U.S.C. 154(b) by 0 days.

(21) Appl. No.: 10/081,178

(22) Filed: Feb. 22, 2002

(65) Prior Publication Data

US 2002/0118792 A1 Aug. 29, 2002

(30) Foreign Application Priority Data

Feb. 22, 2001 (DE) ............................................. 10108633

(51) Int. Cl.⁷ ................................................. H05G 1/28
(52) U.S. Cl. ........................ 378/163; 378/164; 378/207
(58) Field of Search ................................. 378/163, 162, 378/164, 20, 62, 205, 98.12, 208, 207

(56) References Cited

U.S. PATENT DOCUMENTS

| 4,131,802 A | 12/1978 | Braden et al. ................. 378/20 |
| 4,174,481 A | 11/1979 | Liebetruth .................... 378/20 |
| 4,613,983 A | 9/1986 | Yedid et al. ............. 378/98.12 |
| 5,216,700 A | 6/1993 | Cherian ........................ 378/163 |
| 5,239,569 A * | 8/1993 | Saleh et al. .................. 378/163 |
| 5,347,570 A | 9/1994 | Haaks ...................... 378/98.12 |
| 5,479,470 A * | 12/1995 | Stenfors ....................... 378/196 |
| 6,097,833 A * | 8/2000 | Lobregt et al. ............. 382/130 |

FOREIGN PATENT DOCUMENTS

| DE | 199 17 867 | 11/2000 | ........... A61B/19/00 |
| DE | 199 58 407 | 6/2001 | ............ A61B/6/00 |

* cited by examiner

Primary Examiner—Edward J. Glick
Assistant Examiner—Courtney Thomas
(74) Attorney, Agent, or Firm—Schiff Hardin & Waite

(57) ABSTRACT

In a method applied and an x-ray system for determining a spatial relationship of X-ray datasets measured independently of one another, an x-ray apparatus registers X-ray datasets of a patient and a scale is provided that makes position data available that are identifiable in at least one of the registered dataset. The position data serve for the determination of the spatial relationship between at least two X-ray datasets that were registered from different body portions of the patient.

17 Claims, 2 Drawing Sheets

APPARATUS AND METHOD FOR DETERMINING THE SPATIAL RELATIONSHIP OF X-RAY DATASETS REGISTERED INDEPENDENTLY OF ONE ANOTHER

BACKGROUND OF THE INVENTION

1. Field of the Invention

The present invention is directed to an X-ray system for the registration of X-ray datasets of a patient as well as to a method for determining the spatial relationship of X-ray datasets at a patient that are measured independently of one another.

2. Description of the Prior Art

Among other things, mobile C-arm x-ray apparatus with which regions of the patient can be radiologically acquired are utilized for medical or surgical interventions at a patient. As a result of this data acquisition, three-dimensional x-ray exposures can be acquired and presented on a picture screen. The reconstructed volume that can be presented with such three-dimensional x-ray data sets currently amounts to approximately $(12 \text{ cm})^3$.

In many instances, however, a number of regions of the patient must be acquired that are spatially separated from one another. Since the x-ray data sets acquired in this way must be placed into a spatial relationship with each another for specific surgical interventions, an exact knowledge of the spacial positions of the individual x-ray data sets is required.

An example of this is a surgical intervention at the knee of a patient in the case of total knee replacement. Here, three-dimensional x-ray exposures (x-ray data sets) of the knee, the ankle and the hip are required, and their spatial relationship relative to one another must be known in order to be able to acquire the correct attitudinal and angular position of the knee joint.

German OS 199 17 867 discloses a method and an apparatus for positional allocation of a treatment devices to an x-ray exposure. The determination of the position data of the treatment region ensues with a camera-assisted navigation system and with the assistance of a reference structure simultaneously acquired with an x-ray exposure of the treatment region. A number of x-ray exposures of different regions of the treatment region can be compiled to form an overall image. A referencing device attached directly to the patient allows the patient to move between two x-ray exposures since this referencing device can be tracked by the navigation system.

SUMMARY OF THE INVENTION

An object of the present invention is to provide an x-ray system and a method employable with an x-ray system that, in a simple way and with little apparatus outlay, enable the exact determination of the spatial relationship between at least two x-ray data sets that were registered at different body segments of a patient.

This object is inventively achieved in an x-ray system and method according to a first embodiment of the invention wherein a scale is attached in the region wherein the x-ray data sets are registered and is visible in the registered x-ray data sets. The scale is rigidly attached in relationship to the patient and is visible in all registered x-ray data sets.

The scale, for example, can be attached to the patient directly or can be integrated in the operating table on which the patient lies during the intervention. In any case, the scale must be attached such that it is fixed in relationship to the patient.

This object also is achieved in a second embodiment of the invention, wherein the acquired spatial relationship of the registered x-ray data sets relative to one another is calculated and/or processed automatically by a processing device.

The automatic processing of the spatial acquired relationship by the processing device has the advantage that these relationships not only can be presented as information for the surgeon, but also can serve as a basis for further calculations. In this way, thus, an enlargement of the volume of the registered three-dimensional x-ray data sets can be achieved. To that end, a number of three-dimensional x-ray data sets are registered that spatially adjoin one another or spatially overlap one another slightly, and these are joined by the processing device and displayed on the picture screen.

DESCRIPTION OF THE PREFERRED EMBODIMENTS

Figure 1:
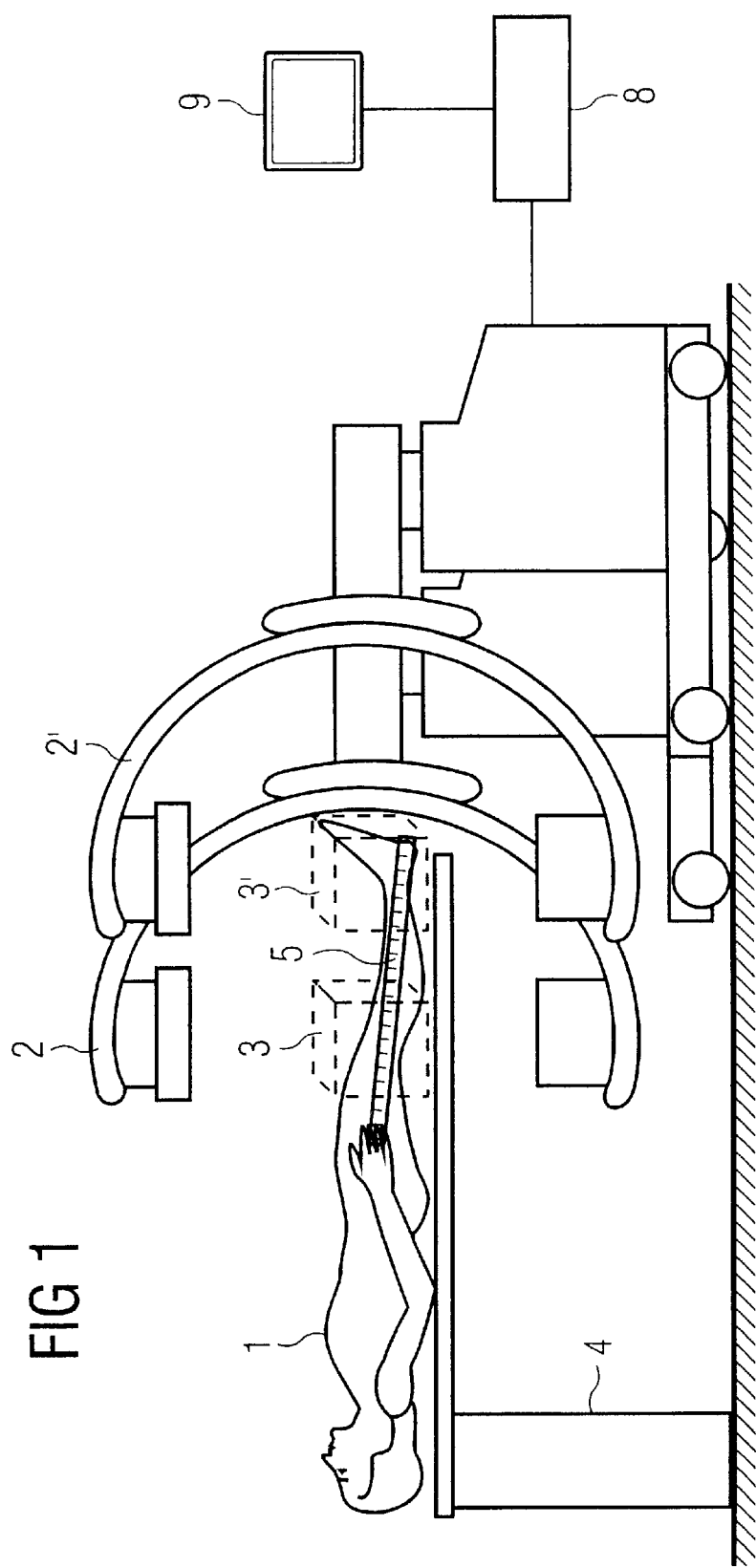
FIG. 1 is an illustration of the inventive x-ray system according to the first embodiment of the present invention.

The functioning of a C-arm x-ray apparatus 2 (simply referred to as x-ray apparatus 2 below) and a first embodiment of the present invention are described in detail below on the basis of FIG. 1.

The three-dimensional x-ray data sets are acquired by the x-ray apparatus 2 first registering a number of two-dimensional x-ray images of a specific region of the patient 1 who lies on an operating table 4. The C-arm of the x-ray apparatus 2 registers a number of two-dimensional x-ray images of the specific region (for example, the knee) from different angles. The two-dimensional x-ray data sets acquired in this way are projected into at least one 3-dimensional x-ray data set by a computer using known projection matrices. The three-dimensional region (volume) that can be registered and presented in this way is shown, for example, as a cube 3.

The three-dimensional x-ray data set is then displayed on a display device 9 (picture screen), whereby a user (usually the surgeon carrying out the surgical intervention at the patient 1) can view the registered region of the patient, for example, form different angles of view and/or in different planes.

According to this embodiment of the present invention, a scale 5 visible in x-ray images (x-ray data sets) is introduced into the region that is to be made visible with the x-ray images. The scale 5 need not necessarily be visible in the projected three-dimensional x-ray data sets for the surgeon. It also suffices for the scale 5 to be contained in one or a few x-ray data sets in the registration of the two-dimensional x-ray data sets.

In this case, the scale 5 is not displayed in the projected, three-dimensional x-ray data set; however, the scale 5 can be automatically recognized and processed by the processing device 8 in this way. Visible in the sense of the present invention thus means that the scale is "visible" for the x-ray apparatus 2, i.e. that the scale is contained in at least one 2-dimensional x-ray dataset and the information acquired therefrom thus can be further-processed.

The term "scale" in the sense of the present invention mean markings that have a precisely defined spatial relationship to one another. These can be individual markings that are attached at specific, fixed intervals on the patient 1 or at the operating table 4. However, as shown in FIG. 1, this can also be a type of measuring stick with corresponding markings that are visible in the x-ray datasets. For example, the scale 5 can thereby be imaged in a line or in a two-dimensional grid.

When x-ray datasets are then registered at different positions of the body of the patient 1, then the continuous scale must be recognizable in all positions (for the surgeon and/or for the processing device 8). Due to the spatial position of the scale 5 in the individual 3D volumes 3, 3' in conjunction with a recognizable division, for example in centimeters (cm), on the scale 5, the spatial relationships of the individual three-dimensional exposures (x-ray datasets) can be identified in a simple way. The shifted position of the x-ray apparatus 2 and thus of the registered volume 3 (or reconstructed from the two-dimensional x-ray datasets) are reference 2' and 3' in the Figure.

Preferably, the body of the scale 5 is largely transmissive for x-rays, so that the result of the registered x-ray datasets, and thus the three-dimensional x-ray dataset resulting therefrom, are falsified as little as possible.

The apparatus that implements the calculation of the two-dimensional x-ray datasets into one (or more) three-dimensional x-ray dataset and the processing apparatus 8 of the present invention are advantageously combined in a single device (computer).

Figure 2:
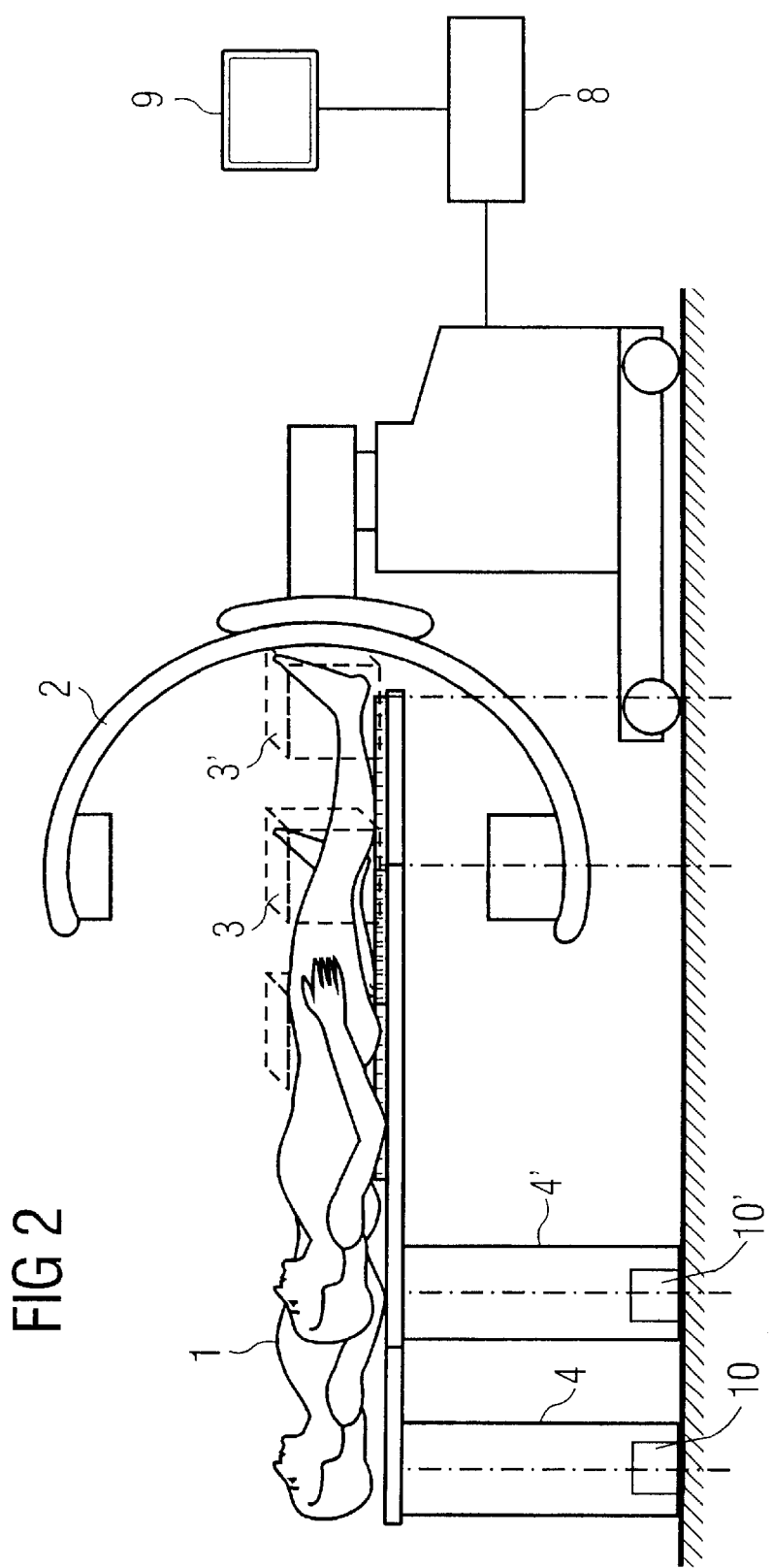
FIG. 2 is an illustration of the inventive x-ray system according to the second embodiment of the present invention.

FIG. 2 is an illustration of the inventive x-ray system according to a second embodiment of the present invention.

The reference characters in FIG. 2 are identical to the reference characters of FIG. 1. In this embodiment of the invention, however, the inventive apparatus for offering position data is integrated in a displaceable/movable operating table 4 for acquiring the motion of the operating table 10 that quantitatively registers the movement of the table. The shifted position of the operating table 4 is symbolized with reference character 4'.

In this exemplary embodiment, the x-ray apparatus 2 does not move relative to the floor, even though it may be a mobile apparatus.

The motion of the C-arm relative to the patient can be determined on the basis of, for example, a scale integrated in the operating table 4 and/or by measuring the table movement. After the registration of the three-dimensional x-ray dataset has ensued at a first position, for example at the knee, the table 4 moves the patient to a second position so that, for example, the hip lies in the isocenter of the C-arm; the C-arm is thereby stationary. The table movement then stops, the traversed distance of the operating table 4 is measured, and another exposure of a three-dimensional x-ray data set ensues (in the example, of the hip)

Although modifications and changes may be suggested by those skilled in the art, it is in the intention of the inventors to embody within the patent warranted hereon all changes and modifications as reasonably and properly come within the scope of their contribution to the art.

We claim as my our invention:

1. An x-ray system comprising:
   an x-ray apparatus for obtaining multiple x-ray datasets of a patient respectively from different body portions of a patient; and
   a scale adapted to be disposed in fixed relationship to the patient, said scale containing scale indications that are visible in at least one of said x-ray datasets, for indicating a spatial relationship between at least two of said x-ray datasets obtained from different body portions of the patient.

2. An x-ray system as claimed in claim 1 wherein said scale is adapted for rigid attachment to the patient.

3. An x-ray system as claimed in claim 1 further comprising an operating table adapted to receive the patient thereon, said scale being attached to said operating table.

4. An x-ray system as claimed in claim 1 wherein said scale comprises a scale body that is substantially transparent to x-rays, on which said scale indications are disposed.

5. An x-ray system as claimed in claim 1 further comprising a processing device for automatically reading said scale indications in said at least one of said x-ray datasets for automatically determining said spatial relationship.

6. An x-ray system as claimed in claim 1 wherein said x-ray apparatus is an x-ray apparatus for obtaining multiple three-dimensional x-ray datasets of a patient respectively from different body portions of the patient.

7. An x-ray system as claimed in claim 1 wherein said x-ray apparatus is movable to respectively different positions for obtaining said multiple x-ray datasets respectively from different body portions, and wherein said scale is visible in each of the respective x-ray datasets obtained with the x-ray apparatus in the respective positions.

8. An x-ray system comprising:
   an operating table adapted to receive a patient thereon, said operating table being selectively positionable;
   an x-ray apparatus for obtaining multiple x-ray datasets of the patient on said operating table respectively from different body portions of the patient, said respective x-ray datasets of said different body portions of the patient being obtained by selectively positioning said operating table; and
   a motion acquisition device for identifying motion of said operating table for determining a spatial relationship between at least two of said x-ray datasets obtained from said different body portions of the patient by quantitatively identifying movement of said operating table relative to said x-ray apparatus between respective exposures for obtaining said at least two x-ray datasets.

9. An x-ray system as claimed in claim 8 further comprising a processor connected to said motion acquisition device for automatically processing said position data to identify said spatial relationship.

10. An x-ray system as claimed in claim 8 wherein said x-ray apparatus is an x-ray apparatus for obtaining multiple three-dimensional x-ray datasets of a patient respectively from different body portions of the patient.

11. A method for determining a spatial relationship of x-ray datasets obtained independently of each other comprising the steps of:
   obtaining multiple x-ray datasets from a patient, respectively from different body regions of said patient;
   providing a scale in fixed relationship to the patient having scale indications thereon which are visible in at least one of said x-ray datasets; and
   determining a spatial relationship between at least two of said x-ray datasets respectively obtained from different body regions from said scale indications in said at least one of said x-ray datasets.

12. A method as claimed in claim 11 comprising automatically identifying said scale indications in said at least one of said x-ray datasets with a processor, and automatically determining said spatial relationship in said processor.

13. A method as claimed in claim 11 wherein the step of obtaining multiple x-ray datasets from a patient comprises obtaining multiple three-dimensional x-ray datasets from a patient.

14. A method as claimed in claim 11 wherein the step of obtaining multiple x-ray datasets from a patient comprises moving an x-ray apparatus to a plurality of different positions for, at each position, obtaining one of said multiple x-ray datasets of the different body region of the patient, and wherein the step of providing a scale in fixed relationship to the patient comprises providing a scale that is visible in each of the x-ray datasets respectively obtained at each of the positions of said x-ray apparatus.

15. A method for determining a spatial relationship of x-ray datasets obtained independently of each other, comprising the steps of:

disposing a patient on a selectively movable operating table;

obtaining multiple x-ray datasets of the patient respectively from different body regions of the patient by irradiating a first body region with x-rays with said operating table positioned at a first position and moving said operating table to a second position and irradiating a second body portion of the patient;

quantitatively measuring movement of said operating table between said first position and said second position; and identifying a spatial relationship between at least two of said x-ray datasets respectively obtained from said different body regions from said quantitative identification of said movement of said operating table.

16. A method as claimed in claim 15 comprising automatically processing said quantitative information representing movement of said operating table in a processor to automatically identify said spatial relationship.

17. A method as claimed in claim 15 wherein the step of obtaining multiple x-ray datasets from a patient comprises obtaining multiple three-dimensional x-ray datasets from a patient.

\* \* \* \* \*